United States Patent
Dahmani

(10) Patent No.: US 12,213,816 B2
(45) Date of Patent: Feb. 4, 2025

(54) RADIATION PROTECTION APPARATUS

(71) Applicant: Siemens Healthineers AG, Forchheim (DE)

(72) Inventor: Chihebeddine Dahmani, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 216 days.

(21) Appl. No.: 18/146,833

(22) Filed: Dec. 27, 2022

(65) Prior Publication Data
US 2023/0210479 A1  Jul. 6, 2023

(30) Foreign Application Priority Data
Dec. 30, 2021  (DE) ..................... 10 2021 215 117.5

(51) Int. Cl.
A61B 6/10     (2006.01)
A61B 6/00     (2006.01)

(52) U.S. Cl.
CPC ............ A61B 6/107 (2013.01); A61B 6/4441 (2013.01)

(58) Field of Classification Search
CPC ....... A61B 6/107; A61B 6/4441; A61B 6/102; A61B 6/547; A61B 6/0407
See application file for complete search history.

(56) References Cited

U.S. PATENT DOCUMENTS

2008/0031422 A1  2/2008  Barkow et al.
2013/0299723 A1  11/2013  Murase et al.

FOREIGN PATENT DOCUMENTS

DE      3012463 C2 *  6/1989
DE    102004039411 A1  2/2006
DE    102010061893 A1  5/2012

OTHER PUBLICATIONS

Reeves, R. R., Ang, L., Bahadorani, J., Naghi, J., Dominguez, A., Palakodeti, V., ... & Mahmud, E., Invasive Cardiologists Are Exposed to Greater Left Sided Cranial Radiation: the Brain Study (Brain Radiation Exposure and Attenuation During Invasive Cardiology Procedures). JACC: Cardiovascular Interventions, 8(9), 1197-1206. (2015); 2015;.

* cited by examiner

*Primary Examiner* — Kiho Kim
(74) *Attorney, Agent, or Firm* — Harness, Dickey & Pierce, P.L.C.

(57) ABSTRACT

A radiation protection apparatus of a medical X-ray imaging system for absorbing scattered X-rays emerging from an examination region, wherein the radiation protection apparatus comprises: a plurality of lead glass elements, wherein each of the plurality of lead glass elements is configured to move between a rest position and a shield position, and also relative to one another. In the shield position, the plurality of lead glass elements form a radiation shield arranged between the examination region and a region occupiable by medical staff.

20 Claims, 4 Drawing Sheets

RADIATION PROTECTION APPARATUS

CROSS-REFERENCE TO RELATED APPLICATION(S)

The present application claims priority under 35 U.S.C. § 119 to German Patent Application No. 10 2021 215 117.5, filed Dec. 30, 2021, the entire contents of which are incorporated herein by reference.

BACKGROUND

In medical imaging via X-rays, a body region of a patient to be examined is irradiated with X-rays generated by an X-ray source. The X-rays penetrate the patient's body tissue, thereby performing specific absorption processes and statistical diffraction and scattering processes with the body tissue for the body tissue in question. The X-rays attenuated by the interactions are detected by an X-ray detector located opposite the X-ray source and at present are typically converted into a digital X-ray image representing the body region of the patient to be examined.

X-ray imaging produces scattered X-rays with an arbitrary beam direction. Therefore, for the most part, the scattered X-rays do not hit the detection surface of the X-ray detector, but bypass it. Therefore, the actual X-ray examination is preferably started or monitored by the staff performing the treatment or operators from outside the examination room in order to protect themselves from scattered radiation. However, in interventional radiology, especially in a catheter laboratory, the staff performing the treatment have to remain in the examination room during X-ray imaging, often very close to the patient. Thus, staff are regularly directly exposed to scattered radiation. Many studies confirm the associated health risk for the staff.

SUMMARY

Various radiation protection apparatuses are known. For example, staff can wear lead-containing radiation protection clothing, such as suits, aprons, coats, helmets or visors during the intervention. Alternatively, independent mobile or ceiling-mounted radiation protection shields or radiation protection screens comprising leaded, but optically transparent, glass panels can be provided in the examination room and these have to be positioned correctly between the patient and the medical staff during imaging.

However, radiation protection clothing is often very uncomfortable and tiring to wear and restricts the freedom of movement of the staff. Moreover, radiation protection clothing is time-consuming to put on and this impedes the medical workflow. In addition, radiation protection clothing does not always protect all body parts of the medical staff. For example, the arms and hands are often still exposed.

Correct (re) positioning of radiation protection apparatuses mounted or provided in the examination room also takes time and disrupts the medical workflow.

Therefore, medical staff are often reluctant to use radiation protection measures. The health risks are accepted.

In contrast, it is an object of one or more example embodiments of the present invention to provide improved radiation protection that is easier to implement. In particular, it is also an object of one or more example embodiments of the present invention to provide radiation protection for automatic and active integration into the medical workflow in a time-efficient manner.

At least this object is achieved by a radiation protection apparatus of a medical X-ray imaging system and the corresponding medical X-ray imaging system according to one or more example embodiments of the present invention and/or the independent claims. Preferred and/or alternative advantageous variants are the subject matter of example embodiments of the present invention and/or the dependent claims.

In a first aspect, one or more example embodiments of the present invention relate to a radiation protection apparatus of a medical X-ray imaging system. The radiation protection apparatus can be formed as a stand-alone unit. However, it preferably works together with the medical X-ray imaging system. Components of the radiation protection apparatus are advantageously formed as parts or components of the medical X-ray imaging system or permanently installed as an integral component thereof.

The radiation protection apparatus is formed to absorb scattered X-rays emerging from an examination region or is suitable for this purpose. To this end, the radiation protection apparatus comprises a plurality of lead glass elements, i.e., at least two lead glass elements, preferably more. The lead glass elements can in each case be formed in the shape of a lamella or sheet. This means that each lead glass element has a sheet-like shape so the extension of a lead glass element in one spatial direction is significantly less than in the other two spatial directions. In particular, the extension of a lead glass element in the shortest spatial direction is at least one order of magnitude shorter than in one of the two other spatial directions. In some embodiments, a lead glass element is in each case formed from glass comprising a percentage of lead or an additional layer of lead or the like. The individual lead glass elements can in each case be moved between a rest position and a shield position. The lead glass elements can simultaneously be moved relative to one another. In the shield position, the lead glass elements form a radiation shield arranged between an examination region and for a region occupied by medical staff.

The examination region preferably comprises the area in which a patient, in particular a body region of the patient to be examined, is arranged for X-ray imaging. Herein, the examination region is penetrated by X-rays. According to one or more example embodiments of the present invention, the examination region comprises an isocenter of the medical X-ray imaging system.

According to one or more example embodiments of the present invention, the medical staff comprises all the people located in the examination room apart from the patient. This includes, for example, medical specialists, such as physicians, assistants, nurses or the like performing an intervention on the patient or medical monitoring of the patient. In addition, the medical staff also comprises operators of the medical X-ray imaging system, who, for example, control the release of radiation, set radiation parameters and/or control an adjustment movement of the medical X-ray imaging system.

According to one or more example embodiments of the present invention, during X-ray imaging, the medical staff are located in the region occupied by the medical staff. This occupied region is located outside the examination region, but preferably close to the examination region. In one embodiment, the occupied region is the area adjacent to the examination region from which the medical staff have good access to the patient or the body region to be examined.

According to one or more example embodiments of the present invention, the lead glass elements can assume a rest position and a shield position. The shield position is assumed when X-ray imaging is performed, i.e., when the medical X-ray imaging system emits X-rays and scattered X-rays can occur. The lead glass elements assume their rest position between the detection of X-ray images, for example during an adjusting movement of the medical X-ray imaging system or intervention-related pauses in the imaging.

An advantage of the radiation protection apparatus according to one or more example embodiments of the present invention is that it can assume a rest position and a shield position. In the shield position, the lead glass elements are positioned relative to one another such that together they form a radiation shield that serves to intercept unwanted scattered X-rays emerging from the examination region. This greatly reduces the amount of scattered X-rays entering the region occupied by the medical staff. On the other hand, in the rest position, the radiation protection apparatus according to one or more example embodiments of the present invention is advantageously small and space-saving.

In this way, the 'footprint', i.e., the space requirement, of a medical X-ray imaging system comprising a radiation protection apparatus according to one or more example embodiments of the present invention only increases slightly in the rest position. Moreover, the accessibility of the examination region is hardly affected by the radiation protection apparatus according to one or more example embodiments of the present invention in phases without X-ray imaging.

In order to achieve a particularly small space requirement, in a preferred embodiment of the present invention, in the rest position, the lead glass elements are arranged congruently with one another in at least one subset. In other words, the lead glass elements are at least partially one above or one behind the other in the rest position. This means that, in the rest position, their base areas are substantially or extensively or completely brought into congruence or overlap. Preferably, since this is particularly space-saving, all lead glass elements of the radiation protection apparatus are arranged congruently with one another in the rest position. In other embodiments of the present invention, the lead glass elements are arranged congruently with one another in the rest position in a first subset and the lead glass elements are arranged congruently with one another in a second subset. Preferably, the first and the second subset of the lead glass elements are equal in size. The two subsets comprise the totality of all lead glass elements. In this way, the radiation protection apparatus according to one or more example embodiments of the present invention can be adapted to the requirements or specifications of various medical X-ray imaging systems and installation situations and a compromise can be achieved with regard to overall length and overall depth.

In one embodiment of the present invention, in the shield position, the lead glass elements span a shield area that substantially corresponds to the sum of the base areas of the lead glass elements. Consequently, in the shield position, the base areas of the lead glass elements form the radiation shield with the shield area. The shield area corresponds to the base area of the radiation shield. In other words, the base areas of the individual lead glass elements in the shield position do not overlap or hardly overlap. In top view, the base areas of the lead glass elements are adjacent to one another. This enables a maximum shield area with maximum shielding effect to be achieved.

In one embodiment of the present invention, the base area of the lead glass elements is triangular or shaped like a sector of a circle. Thus, in the shield position, the lead glass elements form the radiation shield with a shield area that substantially spans a circular sector. Other basic shapes of the lead glass elements, for example a rectangular basic shape, are also possible. Herein, the radiation shield can also be substantially shaped like a sector of a circle, but also substantially have a rectangular or square shape.

In a particularly preferred embodiment, the shield area forms the radiation shield, which spans an angle between 90° and 180°. In this way, it is advantageously possible to form a radiation shield that reliably protects at least one member of the medical staff in the occupied region from scattered X-rays.

In a further embodiment of the present invention, the lead glass elements of the radiation protection apparatus are connected to one another via at least one common axis of rotation and are formed to rotate about this axis of rotation during an adjusting movement between the rest position and the shield position. In a preferred embodiment, lead glass elements with a triangular basic shape or a basic shape in the form of a sector of a circle are penetrated by a common shaft near the corner between their two longest outer sides, said shaft running along the axis of rotation. The adjusting movement of the individual lead glass elements is preferably achieved by rotation of the shaft. For this purpose, at least one of the lead glass elements is coupled to the shaft accordingly. The adjustment path or angle of rotation of the individual lead glass elements is preferably of different lengths so that they span the radiation shield in a fan-like manner when they are brought into the shield position.

In embodiments with a first and a second subset or more subsets of lead glass elements, two or more common axes of rotation or shafts can be provided about which in each case the lead glass elements of the associated subset rotate in order to change between the rest position and the shield position.

In a preferred embodiment of the present invention, the radiation protection apparatus comprises 5 to 25 lead glass elements. In some embodiments of the present invention, a lead glass element has a thickness/height (extension perpendicular to the base area) in a range of 5 mm to 15 mm, preferably a thickness of 7 mm to 11 mm, particularly preferably 8 mm. According to one or more example embodiments of the present invention, the number of lead glass elements can be used to adapt the overall depth (substantially the number of lead glass elements×thickness) of the radiation protection apparatus to specifications of a medical X-ray imaging system. If the overall depth or the number of lead glass elements is reduced, the width of the lead glass elements is advantageously increased in order to continue to achieve a necessary width of the shield area or the desired angular range of 90° to 180° of the radiation shield shaped like a sector of a circle.

Particularly preferred embodiments of the radiation protection apparatus according to the present invention comprise lead glass elements with a longitudinal extension in a range between 200 mm and 500 mm. With respect to the triangular or circular sector shape of the base area of the lead glass elements, the longitudinal extension describes the length of the longest side of the triangle or the radius of the circular sector. In this way, the radiation shield is formed with a maximum height of 500 mm and a maximum width of 1000 mm. This area is well adapted to protect at least one member of the medical staff in the occupied region reliably from scattered X-rays.

In some embodiments, for optimum support of a medical workflow, the radiation protection apparatus according to the present invention comprises at least one drive unit for moving the lead glass elements between the rest position and the shield position. The drive unit is preferably formed as a motor unit, in particular as an electric motor. It preferably comprises a rotary motor, the drive shaft of which forms the common shaft of the lead glass elements or is coupled thereto. In alternative embodiments, the drive unit comprises a linear motor in order to adjust the individual lead glass elements linearly.

On the one hand, all lead glass elements can be operatively connected to the common shaft and driven thereby. In an alternative embodiment, the shaft only drives the lead glass element with the longest adjustment path, wherein the other lead glass elements are inevitably also moved indirectly between adjacent lead glass elements, for example via textile coupling elements.

The drive unit supports automated actuation of the radiation protection apparatus. The drive unit can, for example, be activated manually by medical staff by pressing a button in order to bring the radiation protection apparatus into the shield position or the rest position.

Alternatively or additionally, the drive unit can be operated fully automatically, for example via control signals generated by a control unit. The control unit can be formed as a component of the radiation protection apparatus according to one or more example embodiments of the present invention and/or as part of a control unit of a medical X-ray imaging system. In the latter case, the common control unit can cause the X-ray imaging system and the radiation protection apparatus according to one or more example embodiments of the present invention to act together or in coordination with one another.

In fully automatic operation of the radiation protection apparatus according to one or more example embodiments of the present invention, user input is no longer required to move the radiation protection apparatus between the rest position and the shield position. The radiation protection apparatus is automatically adjusted between the shield position and the rest position. The automatic actuation of the radiation protection apparatus is optimally integrated into the medical workflow. The medical staff can now concentrate fully on the medical workflow without having to dispense with radiation protection.

The automated operation of the radiation protection apparatus according to one or more example embodiments of the present invention is described in more detail below with respect to the medical X-ray imaging system according to one or more example embodiments of the present invention.

In order to optimally adapt the radiation protection apparatus or the shielding effect thereof to a variable position of a member of the medical staff within the occupied region, in a further embodiment, the radiation protection apparatus is further equipped with a guide apparatus with at least one guide rail, wherein the guide apparatus is formed to adjust the lead glass elements and the drive unit along the guide rail. Therefore, the guide apparatus is formed to adjust the position of the radiation shield along the guide rail. For this purpose, the guide apparatus can comprise a second drive unit, for example in the form of an electromotive linear drive. Alternatively, the guide apparatus can be formed for manual adjustment of the radiation protection apparatus, for example in that an adjusting lever is provided via which the radiation protection apparatus can be moved along the guide rail. Moreover, locking means can be provided on the guide rail via which the radiation protection apparatus can be fixed in a desired position along the guide rail.

The proposed radiation protection apparatus according to one or more example embodiments of the present invention implements an automated, in particular fan-like, radiation protection screen made of leaded glass elements or glass lamellas. The radiation protection apparatus can be arranged at various locations in the examination room, preferably on a medical X-ray imaging system. In some embodiments, its position can also be subsequently adapted via a corresponding guide apparatus. For example, the radiation protection apparatus according to one or more example embodiments of the present invention can be attached to an X-ray detector and/or to a patient bench of a medical X-ray imaging system and spanned out for, or during, the detection of X-ray image data in order to shield the scattered radiation.

The proposed radiation protection apparatus can be operated fully automatically and, in some embodiments, eliminates the need for the active involvement of medical staff, as is required, for example, with conventional ceiling-mounted lead glass panels. In this sense, the spanning out of the radiation shield can no longer be 'inadvertently' forgotten, since it can be automatically activated and deactivated. This also reduces adverse effects on the medical staff during the medical procedure. The radiation protection apparatus as such can further be offered as a retrofit option for a medical X-ray imaging system that is already installed.

In a further aspect, one or more example embodiments of the present invention relate to a medical X-ray imaging system as such comprising at least one radiation protection apparatus. In other words, the medical X-ray imaging system according to one or more example embodiments of the present invention can also comprise two or more radiation protection apparatuses. The radiation shields formed in each case can then work together for optimized radiation protection. In a preferred embodiment, the at least one radiation protection apparatus is permanently installed as an integral component of the medical X-ray imaging system. Components of the medical X-ray imaging system can form or integrate components of the radiation protection apparatus.

The medical X-ray imaging system uses X-rays to generate medical image data of a patient or a body region of the patient to be examined. For this purpose, the medical X-ray imaging system comprises at least one X-ray source for generating X-rays and an X-ray detector for detecting the X-rays that have penetrated the patient or the body region to be examined. Optionally, to support the patient, a patient bench with a supporting surface can be provided on which the patient is supported for X-ray imaging. Consequently, the medical X-ray imaging system can be formed as a conventional radiography system, i.e., as a fluoroscopy system, mammography system, C-arm system or angiography system or computed tomography system.

Preferably, the medical X-ray imaging system comprises a radiation protection apparatus according to one or more example embodiments of the present invention, which is arranged on the patient bench and/or on the X-ray detector.

In a preferred embodiment, the medical X-ray imaging system is formed as a C-arm X-ray system. As described above, it comprises a patient bench, an X-ray source and an X-ray detector. Here, the X-ray source and the X-ray detector are arranged at opposite ends of a C-arm in such a way that the X-ray source emits the generated X-rays in the direction of the X-ray detector. The patient bench is arranged between the X-ray source and X-ray detector and forms a supporting surface for supporting the patient on which the patient is supported penetrating the isocenter of the X-ray system in the examination region of the X-ray system. The C-arm X-ray system comprises a radiation protection apparatus arranged at a longitudinal edge of the patient bench and, in the shield position, spans a shield area perpendicular to the supporting surface of the patient bench.

Therefore, the radiation shield formed by the radiation protection apparatus stands vertically upward on a longitudinal outer side of the patient bench when the patient bench is aligned horizontally thus separating the examination region from the region occupied by the medical staff.

If the radiation protection apparatus also comprises a guide apparatus, in the above embodiment, this preferably extends along the longitudinal edge of the patient bench. This advantageously enables the position of the radiation protection apparatus or the radiation protection effect thereof to be shifted along the longitudinal side of the patient bench in order to adapt to a body region of the patient to be examined, for example the head, abdomen or lower abdomen.

Alternatively or additionally, the medical X-ray imaging system according to one or more example embodiments of the present invention can comprise a second radiation protection apparatus. This is preferably arranged on the X-ray detector and supplements the radiation protection effect of the radiation protection apparatus arranged on the patient bench. The structure, dimensions and functionality of the two radiation protection apparatuses can differ from one another, but they each correspond to one of the variants described in the introduction.

In a further preferred embodiment, the medical X-ray imaging system according to the present invention comprises a sensor unit formed to detect angulation of the C-arm. Herein, the angulation describes the angular position of the C-arm relative to a floor of the examination room or to the supporting surface of the patient bench. The X-ray imaging system further comprises a control unit formed to generate control signals for the drive unit of the radiation protection apparatus based on the detected angulation.

This embodiment is based on the knowledge that the region occupied by the medical staff is exposed to scattered radiation to varying degrees. With high angulation (X-ray exit direction is close to the horizontal), more scattered X-rays hit the occupied region. With low angulation (X-ray exit direction is close to the vertical), the occupied region is less affected by scattered X-rays.

If the angulation of the C-arm is taken into account when the radiation protection apparatus is actuated, automatic use of the radiation protection apparatus is advantageously only targeted when radiation protection is actually required. Otherwise, the radiation protection apparatus remains in its rest position and does not impede the workflow. Moreover, taking account of angulation also enables the base area of the radiation shield to be adapted to the requirements of specific X-ray imaging. The maximal possible shield area is not necessary in every case.

The sensor unit can comprise one or more sensors configured to detect the angulation of the C-arm. The sensor can, for example, be formed as a three-dimensional camera that monitors the C-Arm visually and ascertains an angular position from the three-dimensional image data on the basis of a model. Alternatively or additionally, position sensors installed as standard in the drive train of the C-arm can be comprised by the sensor unit and in each case, alone or together, determine the angular position of the C-arm using their current position data. In some embodiments, the sensor unit is advantageously in data communication with a control unit of the medical X-ray imaging system and transmits the sensor data describing the angulation and/or the angulation to the control unit.

The control unit basically controls an adjusting movement of the at least one radiation protection apparatus by generating control signals for the drive unit of the at least one radiation protection apparatus, for example based on a previously stored or defined look-up table or via user commands received via an operator interface, for example an operating button. According to one or more example embodiments of the present invention, the control unit is formed to adapt the control signals for the or the adjusting movement of the radiation protection apparatus based on the angulation of the C-arm. In other words, the control unit comprises control logic or a computing rule that takes the angulation of the C-arm into account and ascertains a position of the individual lead glass elements dependent thereon and generates and transmits corresponding control signals for the drive unit of the at least one radiation protection apparatus.

The control unit is advantageously formed as a part or module of the computing unit of the medical X-ray imaging system. The computing unit is inter alia used to control the X-ray imaging process and/or to further process the acquired detector data or to reconstruct X-ray image data from the acquired detector data. The computing unit and control unit can be arranged in the medical X-ray imaging system. Alternatively, the computing unit can also be arranged remotely or separately. The control unit is formed to generate control signals for the drive unit of the at least one radiation protection apparatus, preferably both radiation protection apparatuses, based on the angulation of the C-arm. Alternatively, a separate control unit can be comprised for each radiation protection apparatus. The control unit is formed to generate control signals for the drive unit, for example based on the angulation of the C-arm detected by the sensor, for example using a look-up table. Herein, the look-up table can, for example, contain in each case differently worded retrievable control command specifications for different angular positions. When the control signals are generated, it is possible for further parameters, for example parameters of the selected X-ray imaging protocol or parameters describing the patient anatomy, to be taken into account by the control unit.

The control unit further comprises an interface unit, via which data communication can take place in both directions with a user interface, with the sensor unit, with other modules of the computing unit of the medical X-ray imaging system and/or the drive unit of the at least one radiation protection apparatus.

In a further embodiment of the present invention, the control unit is also formed to control the guide apparatus and in particular the drive unit thereof and to generate control signals therefor in order to adapt the position of the radiation protection apparatus, specifically the position of the lead glass elements and the drive unit of the radiation protection apparatus along its at least one guide rail. Here, the control unit can also take account of parameters of the selected X-ray imaging protocol or parameters describing the patient anatomy or the like by the control unit.

In a further advantageous embodiment of the present invention, the sensor unit of the medical X-ray imaging system further comprises a proximity sensor formed to detect a distance between the radiation protection apparatus and a moving object. According to one or more example embodiments of the present invention, a moving object is a member of the medical staff, the actual patient or a medical device or instrument or a moving part of the actual medical X-ray imaging system, which is located in the examination region or the occupied region and is not stationary. The control unit is correspondingly formed to check whether the distance is below a predefined minimum distance (or minimum threshold) and, if the distance is below the minimum distance, to generate control signals for the drive unit of the radiation protection apparatus in order to bring the radiation protection apparatus into the rest position.

In this way, it is advantageously possible to prevent an undesirable collision and any resulting damage to the radiation protection apparatus and/or injuries to people.

The proximity sensor can, for example, also be formed as a three-dimensional camera that monitors the radiation protection apparatus and whose image data enables conclusions to be drawn regarding the distance to a moving object. Alternatively, a proximity sensor, for example in the form of a capacitive or inductive proximity sensor, can be formed close to the radiation protection apparatus. The minimum distance can, for example, be a few centimeters, for example 10 cm, or more. The control unit is correspondingly formed to execute a program routine which compares the stored minimum distance with the detected distance and provides for the generation of a control signal for adjusting the lead glass elements into the rest position if the distance is below the minimum distance.

If there is a risk of collision, the rest position of the radiation protection apparatus is assumed as quickly as possible without the need for user input and corresponding permanent user monitoring.

The rest position, i.e., the space-saving position of the radiation protection apparatus, is also automatically assumed when X-ray imaging has been completed. In particular, the rest position is also assumed when the angulation of the C-arm or, more generally, the position of the medical X-ray imaging system is changed or the X-ray imaging is completed. Preferably, the radiation protection apparatus is stowed with at least partially congruent lead glass elements along the X-ray detector edge or the longitudinal side of the patient bench.

In summary, the spanning out of the radiation protection apparatus can be activated and/or deactivated depending on the angulation of the C-Arm or more generally in dependence on the position or location of the medical X-ray imaging system. Moreover, the X-ray imaging system according to one or more example embodiments of the present invention provides collision monitoring in order to protect medical equipment and people.

BRIEF DESCRIPTION OF THE DRAWINGS

The above-described properties, features and advantages of this invention and the manner in which they are achieved will become clearer and more plainly comprehensible in conjunction with the following description of exemplary embodiments explained in more detail in conjunction with the drawings. This description does not restrict the present invention to these exemplary embodiments. In different figures, the same components are given identical reference symbols. The figures are generally not to scale. The drawings show.

DETAILED DESCRIPTION

Figure 1:
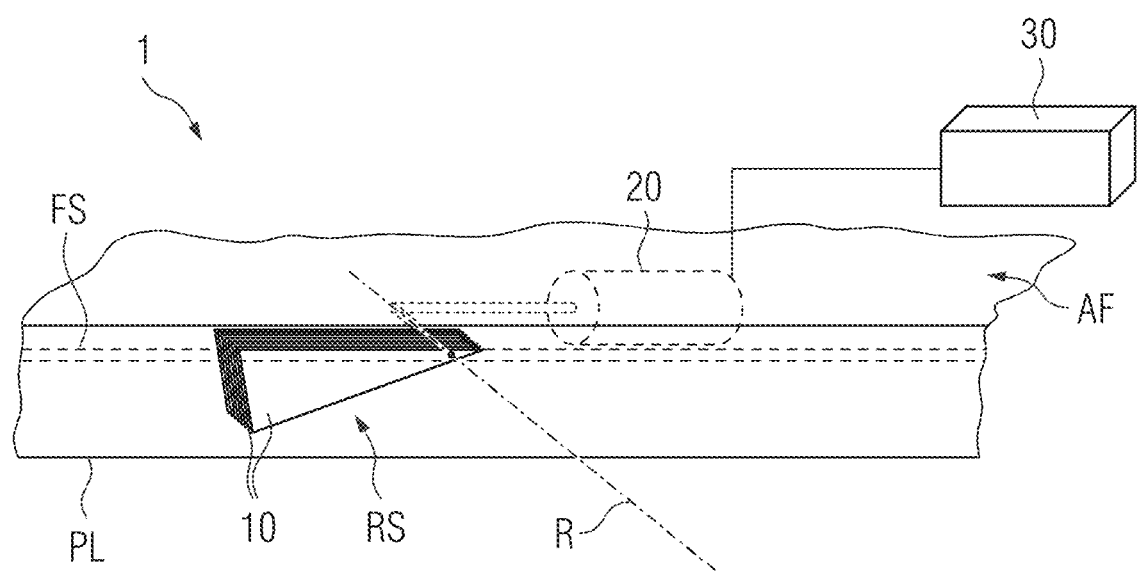
FIG. 1 a view of a radiation protection apparatus according to the present invention in a first exemplary embodiment in the rest position, FIG. 2 a view of the radiation protection apparatus according to the present invention according to the first exemplary embodiment in the shield position, FIG. 3 a view of a radiation protection apparatus according to the present invention in a second exemplary embodiment in the rest position, FIG. 4 a view of the radiation protection apparatus according to the present invention according to the second exemplary embodiment in the shield position, FIG. 5 a view of a medical imaging system in the form of a C-arm X-ray system according to an embodiment of the present invention with two radiation protection apparatuses in the rest position, FIG. 6 a view of a medical imaging system in the form of a C-arm X-ray system according to the embodiment in FIG. 5 with two radiation protection apparatuses in the shield position, and FIG. 7 a view of a medical imaging system in the form of a C-arm X-ray system in a further embodiment of the present invention with a radiation protection apparatus in the shield position.

FIG. 1 shows a view of a radiation protection apparatus 1 according to the present invention in a first exemplary embodiment in the rest position RS.

Figure 2:
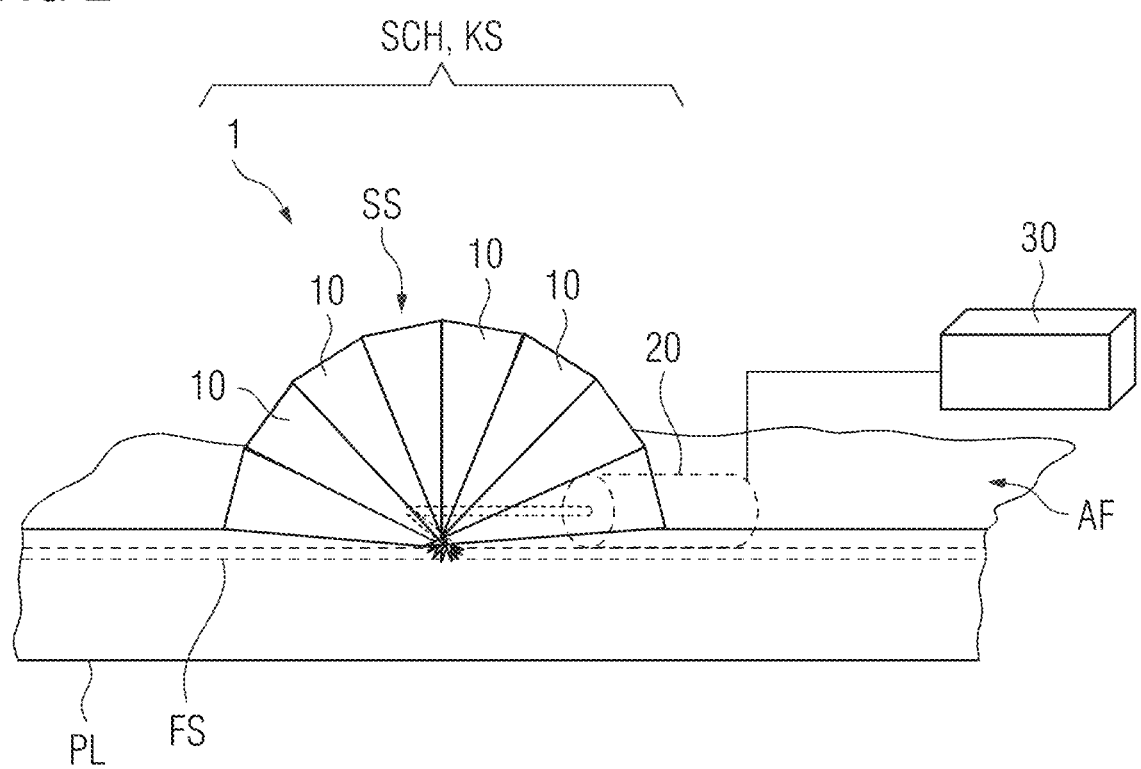

FIG. 2 shows a view of the radiation protection apparatus 1 according to the present invention according to the first exemplary embodiment in the shield position SS.

The radiation protection apparatus 1 is arranged on a patient bench PL of a medical X-ray imaging system 100. The patient bench PL forms a supporting surface AF at its upper side for receiving a patient. The patient is arranged on the supporting surface AF in an examination region U between an X-ray source RQ and an X-ray detector RD of the medical X-ray imaging system 100 (see FIG. 5). The examination region U is penetrated by X-rays emitted by the X-ray source RQ to generate X-ray image data. Herein, scattered X-rays also occur and are propagated in an arbitrary spatial direction and only partially hit the X-ray detector RD. The radiation protection apparatus 1 is used to absorb these scattered X-rays emerging from the examination region U. It comprises a plurality of lead glass elements 10, in the present case, it comprises eight lead glass elements 10. In principle, the radiation protection apparatus 1 according to an embodiment of the present invention can comprise five to 25 lead glass elements. In embodiments in which lead glass elements 10 at least partially overlap in the rest position RS, the number and the embodiment of the lead glass elements 10 can be used to vary the overall depth of the radiation protection apparatus 1 and adapt it to the specifications of the medical X-ray imaging system 100.

The lead glass elements 10 are arranged here in their rest position RS in which they are all arranged in congruence to save space, i.e., with their base areas overlapping one another and moreover substantially parallel to a longitudinal edge surface of the patient bench PL. In this embodiment, in the rest position RS, the radiation protection apparatus does not require any space that protrudes vertically over the patient bench PL. However, the lead glass elements 10 can also be brought or adjusted into a shield position SS, as shown in FIG. 2. For this purpose, the lead glass elements can be moved relative to one another or also relative to the patient bench PL. In the shield position SS, the lead glass elements 10 form a radiation shield SCH arranged between the examination region U and an occupied region A (see FIG. 5) for medical staff. In the shield position SS, the radiation protection apparatus 1 according to the an embodiment of the present invention protects the medical staff (not shown), a physician, a medical assistant, an operator of the medical imaging system or the like, from the scattered X-rays during X-ray imaging.

In this embodiment, the lead glass elements 10 of the radiation protection apparatus 1 are all connected to one another via a common axis of rotation R. They are formed to rotate about this axis of rotation R during an adjusting movement between the rest position RS and the shield position SS. In this embodiment, a drive shaft (not shown) which is coupled in a fixed manner to the individual lead glass elements 10 extends congruently to the axis of rotation R and moves the lead glass elements 10 relative to one another by rotation until each lead glass element 10 has reached its shield position SS.

To execute the rotational movement, the radiation protection apparatus 1 shown here comprises a drive unit 20 in the form of an electromotive rotary drive. The drive shaft of the motor is coupled in a manner known per se to the common shaft of the lead glass elements 10 in order to set them in rotation.

The drive unit can be in data communication with a control unit 30 to receive control signals, as will be explained in more detail with reference to FIGS. 5 to 7.

In this embodiment, in the shield position SS, the lead glass elements 10 span a shield area that substantially corresponds to the sum of the base areas of the lead glass elements 10. Only the part of the base area penetrated by the common drive shaft remains in congruence in the shield position SS. In the embodiment shown here, the base areas of the lead glass elements 10 are triangular. The shield area of the radiation shield SCH substantially spans a circular sector KS, wherein here the radiation shield SCH spans an angle of approximately 175°.

In the present case, the lead glass elements 10 have a longitudinal extension of 40 cm. Thus, the radiation shield SCH is approximately 70 cm to 80 cm wide and just under 40 cm high. The upper body and head of at least one member of the medical staff who has to remain close to the patient during X-ray imaging can thus be effectively protected from the scattered X-rays.

In the embodiment shown here, the radiation protection apparatus also comprises a guide apparatus with at least one guide rail FS, here two guide rails. In the present case, the guide rails are arranged along the longitudinal edge of the patient bench PL and substantially extend over the entire length of the patient bench PL. The guide apparatus is used to adjust the lead glass elements 10 together with the drive unit 20 along the longitudinal side of the patient bench and thus to flexibly adapt the position of the radiation protection apparatus 1 relative to the patient or to the body region to be examined. The guide apparatus advantageously also comprises a drive unit (not shown) in the form of an electromotive linear drive. For example, drive unit 20 and the common shaft of the lead glass elements 10 can be attached to a carriage arranged in the patient bench PL and which is adjustably mounted along the guide rails FS by the linear motor.

Otherwise, reference is made to the further figures.

Figure 3:
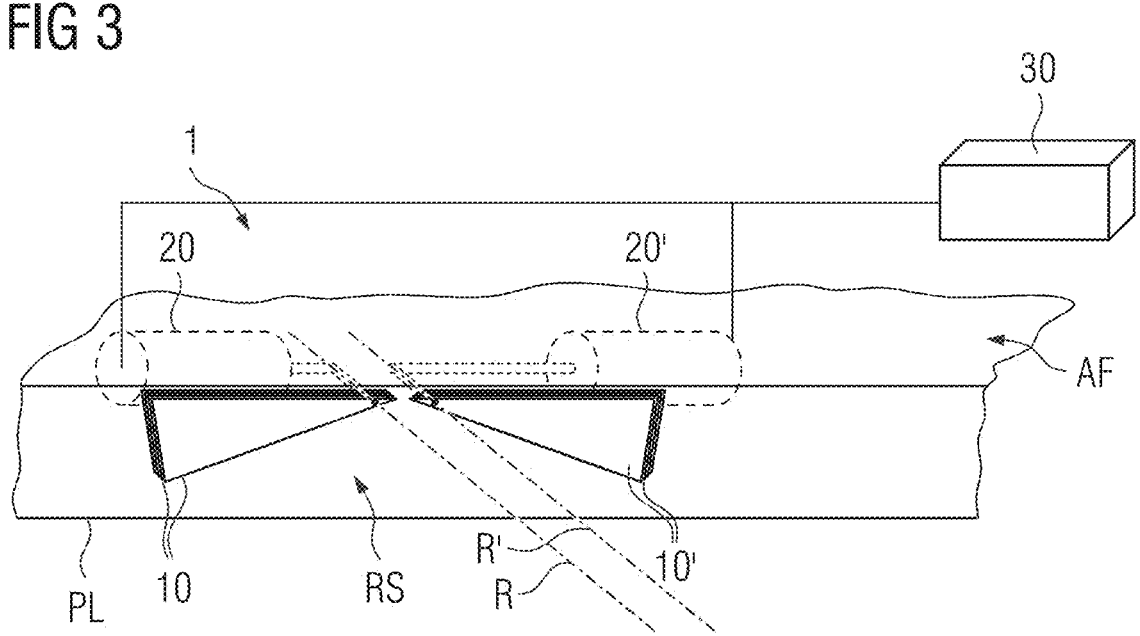

FIG. 3 shows a view of a radiation protection apparatus 1 according to the present invention in a second exemplary embodiment of the present in the rest position RS.

Figure 4:
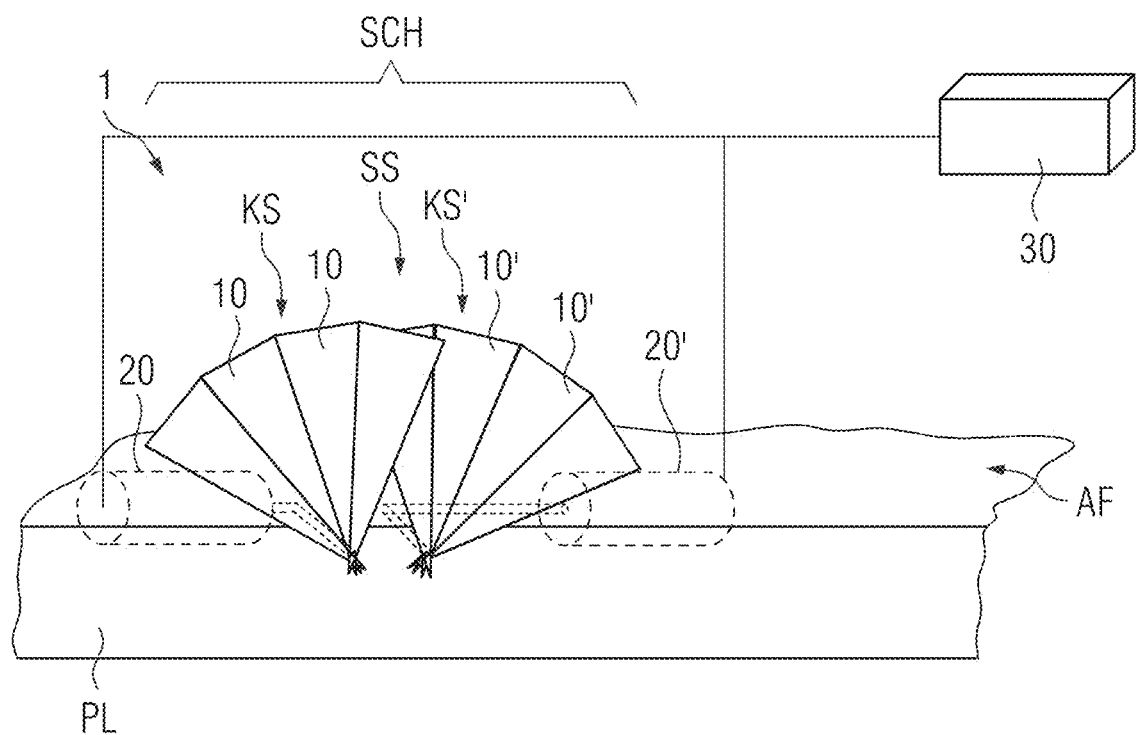

FIG. 4 shows a view of the radiation protection apparatus 1 according to the present invention according to the second exemplary embodiment in the shield position SS.

In this embodiment, the radiation protection apparatus 1 is again arranged on a longitudinal side of a patient bench PL of a medical X-ray imaging system 100. Here, the radiation protection apparatus 1 is again used to absorb the scattered X-rays. Here, it again comprises eight lead glass elements 10.

Here, the eight lead glass elements are divided into two subsets of four lead glass elements 10, 10' each. In the rest position RS, in each case the four lead glass elements 10, 10' in a subset are arranged in congruence to save space. In the rest position, both subsets extend substantially parallel to the longitudinal edge surface of the patient bench PL and, in this embodiment, in the rest position RS, do not require any space that protrudes vertically over the patient bench PL.

This arrangement of the lead glass elements 10, 10' in two subsets lying horizontally along the short axis of the patient bench requires significantly less installation space than the embodiment shown in FIGS. 1 and 2.

Here, the lead glass elements 10 can again be adjusted into the shield position SS, as shown in FIG. 4. For this purpose, the lead glass elements 10, 10' in each subset can be moved relative to one another or also relative to the patient bench PL. In the shield position SS, the lead glass elements 10, 10' form a radiation shield SCH arranged between the examination region U and a region A occupied by medical staff.

Here, the lead glass elements 10, 10' in each subset are connected to one another via a common axis of rotation R, R'. During an adjusting movement between the rest position RS and the shield position SS, they rotate about their respective axis of rotation R, R'. In this embodiment, in each case a drive shaft (not shown) which is only coupled to the lead glass element in a subset with the longest adjustment path extends congruently to the axes of rotation R, R'. Here, the lead glass elements 10, 10' in one subset are connected to one another via textile coupling elements.

In the present case, both shafts are driven by respective drive units 20, 20', again in the form of electric rotary motors. If the lead glass element with the longest adjustment path is now swiveled about the axis of rotation by the drive shaft, the other three lead glass elements in a subset are pulled along by the textile coupling elements until each lead glass element 10 has reached its shield position SS.

Once again, in this embodiment, the two drive units 20, 20' can be in data communication with a control unit 30 in order to receive control signals, as will be explained in more detail with reference to FIGS. 5 to 7.

In this embodiment, in the shield position SS, the lead glass elements 10, 10' again span a shield area that substantially corresponds to the sum of the base areas of the lead glass elements 10, 10'. Here, the base areas of the lead glass elements 10, 10' are once again triangular. The shield area of the radiation shield SCH substantially spans a circular sector KS, wherein here the radiation shield SCH spans an angle of approximately 120°.

In the present case, the lead glass elements 10 have a longitudinal extension of 30 cm. Thus, the radiation shield SCH is approximately 50 cm to 6 cm wide and just under 30 cm high. The upper body of a member of the medical staff who has to remain close to the patient during X-ray imaging can thus be effectively protected from the scattered X-rays. In order also to protect the person's head from scattered X-rays, at least one further radiation protection apparatus can be provided on the medical X-ray imaging system 100 (see FIGS. 5 and 6).

Otherwise, reference is made to the further figures.

Figure 5:
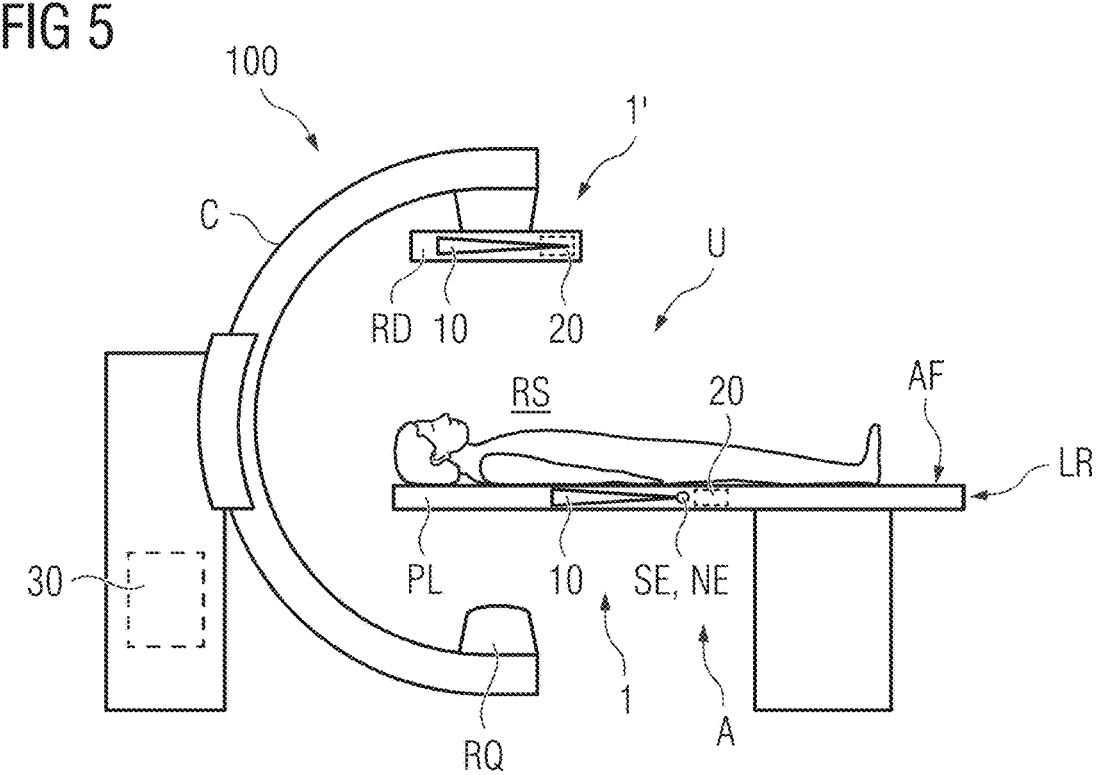

FIG. 5 shows a view of a medical imaging system 100 in the form of a C-arm X-ray system according to an embodiment of the present invention with two radiation protection apparatuses 1, 1' in the rest position RS.

Figure 6:
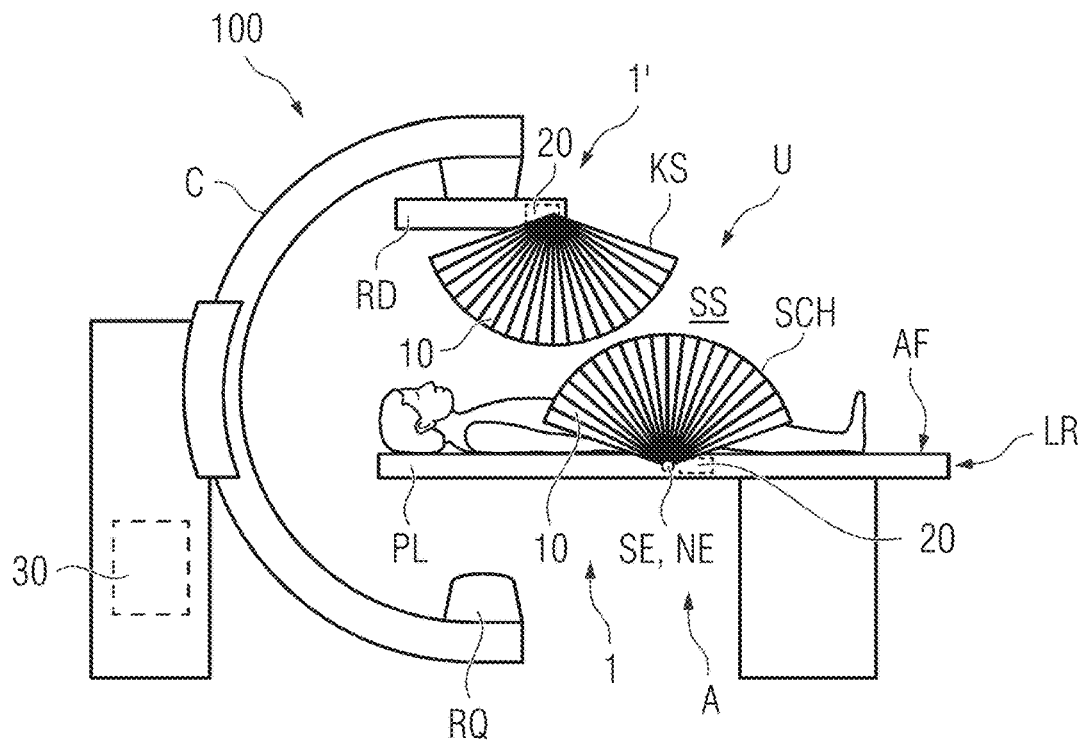

FIG. 6 shows a view of a medical imaging system 100 in the form of a C-arm X-ray system according to the embodiment in FIG. 5 with the two radiation protection apparatuses 1, 1' in the shield position SS.

Figure 7:
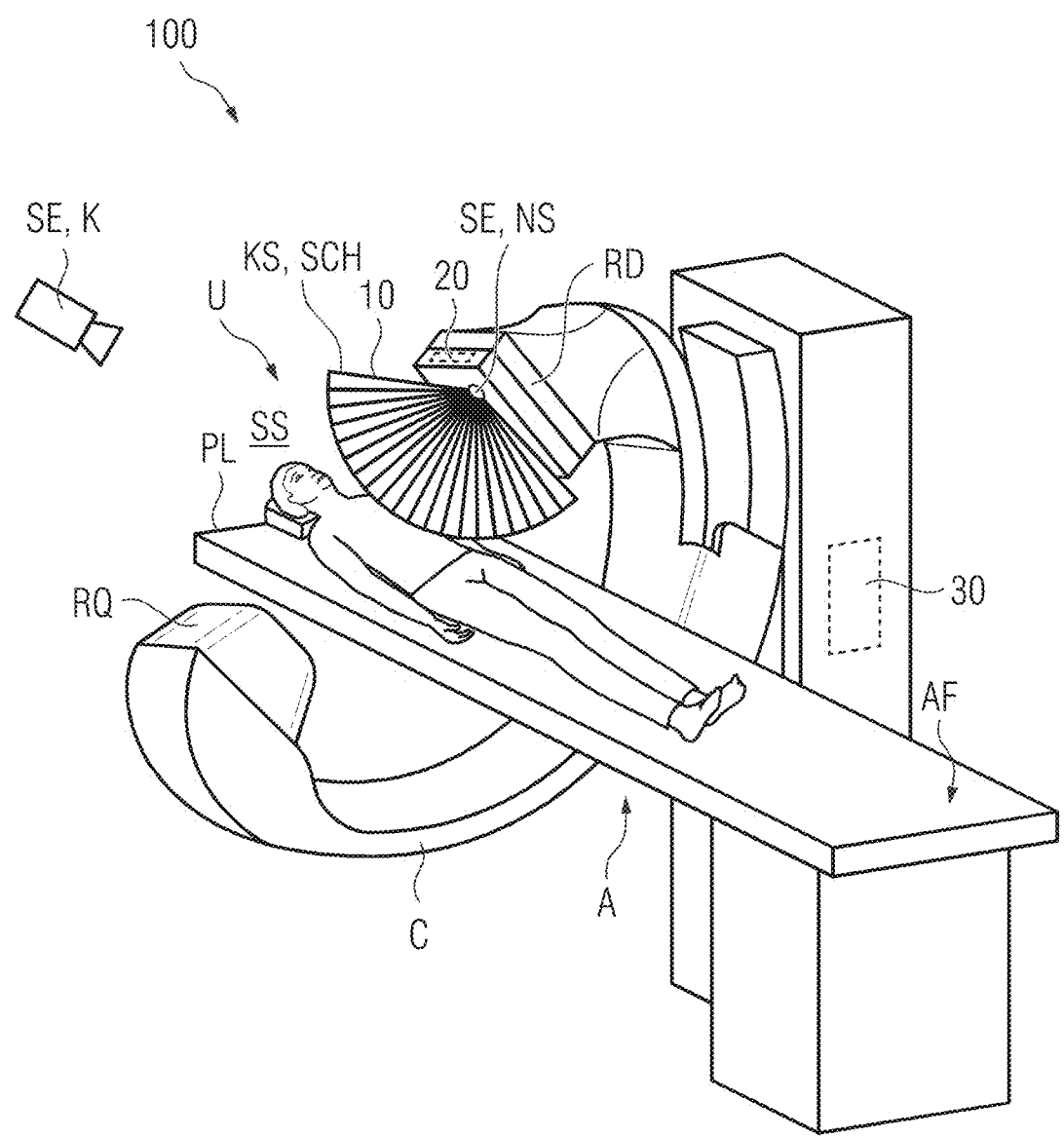

FIG. 7 shows a view of a medical imaging system 100 in the form of a C-arm X-ray system in a further embodiment of the present invention with a radiation protection apparatus 1 in the shield position SS.

The embodiments of a medical X-ray imaging system according to the present invention shown in FIGS. 5 to 7 all comprise at least one radiation protection apparatus 1, 1' according to the present invention, for example formed as described with reference to FIGS. 1 to 4.

In FIGS. 5 to 7, the medical X-ray imaging system 100 is formed as a C-arm X-ray system such as those preferably used for angiography examinations or angiography interventions. However, other embodiments of the medical X-ray imaging system are also conceivable and within the spirit of the present invention.

The medical X-ray imaging system 100 comprises a patient bench PL, an X-ray source RQ and an X-ray detector RD. The X-ray source RQ and X-ray detector RD are arranged at opposite ends of a C-arm C of the system.

In FIGS. 5 and 6, a first radiation protection apparatus 1 is arranged on the longitudinal edge LR of the patient bench PL. In the shield position SS, it spans a shield area perpendicular to the supporting surface AF of the patient bench.

A second radiation protection apparatus 1' is arranged on an outer edge of the X-ray detector RD. This spans a downwardly directed radiation shield SCH that is substantially perpendicular to the detection surface. Here, the first and second radiation protection apparatuses have 24 lead glass elements 10, which in each case are arranged on a common axis of rotation and in each case can be moved via a drive unit 20 between a rest position RS and a shield position, for example as described with reference to FIGS. 1 to 4.

The two radiation protection apparatuses 1, 1' work together to provide effective shielding of the medical staff and simultaneously enable good protection from scattered X-rays in the shield position.

The embodiment of the medical X-ray imaging system 100 shown in FIG. 7 comprises only one radiation protection apparatus 1, which is arranged on the X-ray detector 1 as described in the introduction.

In addition, the C-arm system 100 comprises a sensor unit SE formed to detect angulation of the C-arm. In FIG. 7, the sensor unit SE comprises a three-dimensional camera K that is arranged on a holding arm of a ceiling-suspended intervention monitor of the C-arm system 100 and visually monitors the C-Arm C, the patient and the patient bench PL.

The camera supplies three-dimensional image data from which the angulation, i.e., the angular position of the C-arm, can be derived.

As an alternative to the camera, the sensor unit SE can also comprise one or more position sensors which are permanently installed in the drive train of the C-arm C and use their position data that is output with reference to a fixed reference coordinate system to derive the angulation of the C-arm.

The C-arm system 100 in FIG. 7 further comprises a control unit 30 formed to generate control signals for the drive unit 20 of the radiation protection apparatus based on the detected angulation in order to move it between the rest position RS and the shield position SS. In this way, the C-arm system 100 according to one or more example embodiments of the present invention implements a fully automatic demand-oriented operation of the radiation protection apparatus 1. Manual actuation of the radiation protection apparatus 1 is unnecessary, at least in some embodiments of the present invention. Thus, the control unit 30 supplies control signals for the drive unit 20 in dependence on the angular position of the C-arm C so that it brings the lead glass elements 10 into the shield position SS or rest position RS. During the generation of control signals or control commands, the control unit can further take account of further parameters relating to the X-ray imaging protocol or anatomical parameters of the patient.

The sensor unit SE of the medical X-ray imaging system 100 in FIGS. 5 and 6 further comprises at least one proximity sensor NS. The proximity sensor NS is formed to detect a distance between one of the radiation protection apparatuses 1, 1' and a moving object. The proximity sensor NS is used to prevent collisions, advantageously collisions between one of the radiation protection apparatuses 1, 1' and the patient, medical staff or medical equipment in the examination region U or the like. The proximity sensor can be an optical, inductive, capacitive proximity sensor. In the present case, the proximity sensor NS is positioned close to the axis of rotation of the lead glass elements 10 of the radiation protection apparatus 1. Other arrangements and in particular a plurality of proximity sensors for each radiation protection apparatus are also conceivable.

The proximity sensor NS can alternatively be one or more three-dimensional cameras K, for example, as described with reference to FIG. 7.

In this embodiment, the control unit 30 is formed to check whether the distance between the radiation protection apparatus 1, 1' and a moving object detected by the proximity sensor is below a predefined minimum distance and, if the distance is below the minimum distance, to generate control signals for the drive unit 20 of the radiation protection apparatus 1, 1' in order to bring the radiation protection apparatus into the rest position RS. In this way, collision protection is again implemented fully automatically.

In the embodiments according to FIGS. 5 to 7, the control unit 30 is at least in unidirectional or bidirectional data communication with the at least one drive unit 20 and the sensor unit SE via at least one data interface. The control unit 30 is formed to receive and process sensor signals from the sensor unit SE. It is further formed to generate control commands/control signals corresponding to an activation (assumption of the shield position SS) or deactivation (assumption of the rest position RS) for the radiation protection apparatus 1, 1', specifically the drive unit 20, and to emit them via the interface. In particular, the control unit 30 is formed to determine and emit control commands in dependence on an evaluation of the detected sensor signals.

Here, the control unit 30 and sensor unit SE are formed as part of a system control apparatus or computing unit of the medical X-ray imaging system 100. The control unit 30 can be in the form of hardware or in the form of software. For example, the control unit 30 is formed as an FPGA ("field programmable gate array") or comprises an arithmetic logic unit.

Additionally or alternatively, semi-automatic or manual operation of the radiation protection apparatus can be provided. For example, the radiation protection apparatus 1, 1' can also be actuated via an operator interface, for example by pressing a button, wherein pressing a button causes the control unit 30 to generate a corresponding control signal.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/ DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where not explicitly mentioned, but advisable and in accordance with the sense of the present invention, individual exemplary embodiments, individual partial aspects or features thereof can be combined with one another or exchanged without departing from the scope of the present invention. Advantages of the present invention described with respect to one exemplary embodiment also apply to other exemplary embodiments without being explicitly mentioned.

Although the present invention has been shown and described with respect to certain example embodiments, equivalents and modifications will occur to others skilled in the art upon the reading and understanding of the specification. The present invention includes all such equivalents and modifications and is limited only by the scope of the appended claims.

What is claimed is:

1. A radiation protection apparatus of a medical X-ray imaging system for absorbing scattered X-rays emerging from an examination region, the radiation protection apparatus comprising:
   a plurality of lead glass elements, each of the plurality of lead glass elements configured to move between a rest position and a shield position, and configured to move relative to one another, wherein
      in the shield position, the plurality of lead glass elements form a radiation shield between the examination region and a region occupiable by medical staff.

2. The radiation protection apparatus as claimed in claim 1, wherein, in the rest position, at least a subset of the plurality of lead glass elements are arranged congruently with one another.

3. The radiation protection apparatus as claimed in claim 2, wherein, in the shield position, the plurality of lead glass elements span a shield area that substantially corresponds to a sum of base areas of the plurality of lead glass elements.

4. The radiation protection apparatus as claimed in claim 2, wherein a longitudinal extension of the plurality of lead glass elements is in a range between 20 cm and 50 cm.

5. The radiation protection apparatus as claimed in claim 1, wherein, in the shield position, the plurality of lead glass elements span a shield area that substantially corresponds to a sum of base areas of the plurality of lead glass elements.

6. The radiation protection apparatus as claimed in claim 5, wherein the base areas of the plurality of lead glass elements are triangular and the shield area substantially spans a circular sector.

7. The radiation protection apparatus as claimed in claim 6, wherein the radiation shield spans an angle between 90° and 180°.

8. The radiation protection apparatus as claimed in claim 6, wherein
   the plurality of lead glass elements are connected to one another via a common axis of rotation, and
   the plurality of lead glass elements are configured to rotate about the axis of rotation during movement between the rest position and the shield position.

9. The radiation protection apparatus as claimed in claim 6, wherein
   the plurality of lead glass elements are connected to one another via a common axis of rotation, and
   the plurality of lead glass elements are configured to rotate about the axis of rotation during movement between the rest position and the shield position.

10. The radiation protection apparatus as claimed in claim 1, wherein the plurality of lead glass elements include 5 to 25 lead glass elements.

11. The radiation protection apparatus as claimed in claim 1, wherein a longitudinal extension of the plurality of lead glass elements is in a range between 20 cm and 50 cm.

12. The radiation protection apparatus as claimed in claim 1, further comprising:
    a drive unit configured to move the plurality of lead glass elements between the rest position and the shield position.

13. The radiation protection apparatus as claimed in claim 12, further comprising:
    a guide apparatus with at least one guide rail, wherein the guide apparatus is configured to adjust the plurality of lead glass elements and the drive unit along the guide rail.

14. A medical X-ray imaging system comprising at least one radiation protection apparatus as claimed in claim 1.

15. The medical X-ray imaging system as claimed in claim 14, wherein the medical X-ray imaging system is a C-arm X-ray system, and the medical X-ray imaging system comprises:
    a patient bench;
    an X-ray source; and
    an X-ray detector, wherein
       the X-ray source and the X-ray detector are arranged at opposite ends of a C-arm,
       the radiation protection apparatus is arranged at a longitudinal edge of the patient bench, and
       in the shield position, the radiation protection apparatus spans a shield area perpendicular to a supporting surface of the patient bench.

16. The medical X-ray imaging system as claimed in claim 15, further comprising:
    a second radiation protection apparatus arranged on the X-ray detector.

17. The medical X-ray imaging system as claimed in claim 15, wherein
    a proximity sensor configured to detect a distance between the radiation protection apparatus and a moving object, and
    a controller configured to
       check whether the distance is below a minimum threshold, and
       generate control signals for a drive unit to bring the radiation protection apparatus into the rest position, in response to the distance being below the minimum threshold.

18. The medical X-ray imaging system as claimed in claim 14, further comprising:
    a sensor configured to detect angulation of a C-arm; and
    a controller configured to generate control signals for a drive unit based on the angulation.

19. The medical X-ray imaging system as claimed in claim 18, wherein the sensor includes a proximity sensor configured to detect a distance between the radiation protection apparatus and a moving object, and the controller is configured to check whether the distance is below a minimum threshold, and generate control signals for the drive unit to bring the radiation protection apparatus into the rest position, in response to the distance being below the minimum threshold.

20. The medical X-ray imaging system as claimed in claim 14, further comprising:

a proximity sensor configured to detect a distance between the radiation protection apparatus and a moving object, and a controller configured to check whether the distance is below a minimum threshold, and generate control signals for a drive unit to bring the radiation protection apparatus into the rest position, in response to the distance being below the minimum threshold.

\* \* \* \* \*